United States Patent
Pesola et al.

(10) Patent No.: US 9,696,387 B2
(45) Date of Patent: Jul. 4, 2017

(54) METHOD AND APPARATUS FOR DETERMINING EFFECTS OF TRANSCRANIAL MAGNETIC STIMULATION TO A BRAIN

(71) Applicant: Nexstim Oy, Helsinki (FI)

(72) Inventors: Katja Pesola, Helsinki (FI); Ilkka Autio, Helsinki (FI)

(73) Assignee: Nexstim Oyj, Helsinki (FI)

(*) Notice: Subject to any disclaimer, the term of this patent is extended or adjusted under 35 U.S.C. 154(b) by 0 days.

(21) Appl. No.: 13/823,113

(22) PCT Filed: Oct. 15, 2012

(86) PCT No.: PCT/FI2012/050987
§ 371 (c)(1),
(2) Date: Mar. 14, 2013

(87) PCT Pub. No.: WO2013/054004
PCT Pub. Date: Apr. 18, 2013

(65) Prior Publication Data
US 2014/0249353 A1    Sep. 4, 2014

Related U.S. Application Data

(60) Provisional application No. 61/547,051, filed on Oct. 14, 2011.

(30) Foreign Application Priority Data

Nov. 3, 2011   (FI) .................................. 20116085

(51) Int. Cl.
*A61B 17/52*   (2006.01)
*A61N 2/00*    (2006.01)
(Continued)

(52) U.S. Cl.
CPC ............. *G01R 33/00* (2013.01); *A61N 2/006* (2013.01); *A61N 2/02* (2013.01)

(58) Field of Classification Search
CPC . A61N 2/006; A61N 2/02; A61N 1/40; A61N 1/37229; G01R 33/00;
(Continued)

(56) References Cited

U.S. PATENT DOCUMENTS 5,857,957 A   1/1999  Lin
6,849,040 B2  2/2005  Ruohonen et al.
(Continued)

FOREIGN PATENT DOCUMENTS

CN   1091983 A    9/1994
FI   114613 B    11/2004
(Continued)

OTHER PUBLICATIONS

Litvak et al., "Artifact correction and source analysis of early electroencephalographic responses evoked by transcranial magnetic stimulation over primary motor cortex", NeuroImage 37 (2007) 56-70.*

(Continued)

*Primary Examiner* — Navin Natnithithadha
*Assistant Examiner* — Sunita Reddy
(74) *Attorney, Agent, or Firm* — Seppo Laine Oy

(57) ABSTRACT

The present invention relates generally to a method and apparatus for determining one or more cumulative effects of an application of transcranial magnetic stimulation to the brain of a subject, as well as a method and apparatus of representing same. According to an aspect of certain embodiments of the invention there is provided a method for determining one or more cumulative effects of an application of transcranial stimulation to one or more locations in a brain of a subject comprising the steps of applying multiple (Continued)

transcranial magnetic stimulation pulses to the brain, determining a dose of each of said stimulation pulses, measuring a physical response of the user and determining or approximating an accumulation of said response of said brain for each of said one or more locations in the brain of said subject.

19 Claims, 7 Drawing Sheets

(51) Int. Cl.
 *G01R 33/00* (2006.01)
 *A61N 2/02* (2006.01)
(58) Field of Classification Search
 CPC ....... G01R 33/3415; A61B 5/055; A61B 5/06; H01F 7/202; G06F 17/5009; G06F 2271/09
 USPC .......... 600/9–15, 417; 128/897–899; 702/19; 607/2
 See application file for complete search history.

(56) References Cited

U.S. PATENT DOCUMENTS

| | | |
|---|---|---|
| 7,720,519 B2 | 5/2010 | Ruohonen |
| 2003/0065243 A1 | 4/2003 | Tanner |
| 2003/0073899 A1 | 4/2003 | Ruohonen et al. |
| 2004/0249422 A1* | 12/2004 | Gliner ................ A61N 1/36167 607/58 |
| 2005/0075560 A1 | 4/2005 | Hannula et al. |
| 2005/0107654 A1 | 5/2005 | Riehl |
| 2006/0017749 A1 | 1/2006 | McIntyre et al. |
| 2008/0058582 A1 | 3/2008 | Aho et al. |
| 2008/0161636 A1 | 7/2008 | Hurme et al. |
| 2009/0082690 A1* | 3/2009 | Phillips et al. ................ 600/544 |
| 2010/0185042 A1* | 7/2010 | Schneider ................ A61N 2/02 600/13 |
| 2011/0034822 A1* | 2/2011 | Phillips et al. ................ 600/544 |
| 2011/0130615 A1 | 6/2011 | Mishelevich |

FOREIGN PATENT DOCUMENTS

| | | |
|---|---|---|
| JP | 2003180649 A | 7/2003 |
| WO | WO 2009026386 A1 | 2/2009 |

OTHER PUBLICATIONS

Reeta Korhonen,"Characterizing and removing strong TMS-induced artifacts from EEG" Thesis submitted for examination for the degree of Master of Science in Technology Apr. 21, 2010.Aalto University School of Science and Technology.*

* cited by examiner

METHOD AND APPARATUS FOR DETERMINING EFFECTS OF TRANSCRANIAL MAGNETIC STIMULATION TO A BRAIN

FIELD OF THE INVENTION

This invention relates to a method and apparatus for determining one or more cumulative effects of an application of transcranial magnetic stimulation to the brain of a subject, as well as a method and apparatus of representing same.

BACKGROUND TO THE INVENTION

Within the field of application of the present invention it is possible to stimulate biological tissue such as the brain, the peripheral nervous system, muscles and the heart of a subject by inducing an electric field in the tissue. In terms of magnetic stimulation, the induction of the abovementioned electric field is accomplished by means of a changing magnetic field. It will be appreciated that such an electric field generates an electric current in the conducting tissue which stimulates the tissue. Various different types of methods and apparatus for magnetic stimulation are known in the industry.

The stimulation of a brain by a changing magnetic field is known as transcranial magnetic stimulation (TMS). Transcranial magnetic stimulation is a non-invasive method used to depolarize or hyperpolarize the neurons of a subject's brain. TMS uses electromagnetic induction to induce weak electric currents using a rapidly changing magnetic field; this can cause activity in specific or general parts of the brain with minimal discomfort, allowing the functioning and interconnections of the brain to be studied. A variant of TMS, repetitive transcranial magnetic stimulation (rTMS), has been tested as a treatment tool for various neurological and psychiatric disorders including migraines, strokes, Parkinson's disease, dystonia, tinnitus, depression and auditory hallucinations.

It is known in the industry, that the locations in the brain of a subject which are stimulated are not necessarily those locations of the brain which have received the most cumulative electromagnetic field (EF) exposure. If it is assumed that treatment efficiency correlates with localized cumulative EF exposure, it becomes useful to integrate exposure over time and hit locations, and then visualize the results of the treatment in an intuitive way that provides a more complete picture of the treatment than simply pinpointing the locations of the stimuli.

Conventionally, the determination of the cumulative effects of application of transcranial magnetic stimulation to the brain of a subject is represented through a linear model where the properties of transcranial magnetic stimulation are transformed into dose elements which can be implemented over time. This method is explained in Finnish patent no. FI114613B, which was continued in the U.S. and issued as U.S. Pat. No. 6,849,040, and which is herein incorporated by reference. It is to be appreciated that an issue with said patent is that the effects of decay, where the dose of transcranial magnetic stimulation is applied over time, are not addressed.

In addition, Finnish patent no. FI114613B provides a method of calculating an effective dose comprising integrating cumulative and effective dose applications over the duration of a magnetic stimulation so as to obtain a cumulative result. However, it will be appreciated that an issue with this method is that a threshold value is provided for the magnitude of the stimulus and although a multiplication factor is included, the magnitude of the multiplication factor is dependent on the frequency of the application of the stimulus.

SUMMARY OF THE INVENTION

An object of the invention is to provide a method and apparatus for determining one or more cumulative effects of an application of transcranial magnetic stimulation to the brain of a subject as well as a method of representing same.

According to a first aspect of certain embodiments of the invention there is provided a method for determining one or more cumulative effects of an application of transcranial stimulation to one or more locations in a brain of a subject, said method comprising the steps of:
  applying one or more transcranial stimulation pulses to said one or more locations in said brain; and
  determining an extent of a response of said brain within a predetermined amount of time, through the presence or absence of one or more pre-determined external events at each of said one or more locations;
  mapping said determined response to a mathematical object having an array of variables, each of said variables representing said determined response of said brain at each of said one or more locations.

According to certain embodiments of the invention, said transcranial stimulation is in the form of magnetic stimulation. In a further embodiment of the invention, said transcranial stimulation is in the form of high frequency stimulation, ultra-sound stimulation, optical stimulation, or the like.

According to certain embodiments of the invention, said one or more pre-determined external events include: an electric field resulting from the transcranial stimulation pulse, a tissue current density induced in a brain of said subject, a density of energy of an electromagnetic field dissipated per unit volume at said one or more locations in the brain of said subject, an increase in temperature at said one or more locations, or a specific rate of absorption at said one or more locations.

According to certain embodiments of the invention, said electric field is expressed as a measure of electric potential difference in relation to a measure of a distance or extent of said electric field in the brain of said subject. In an embodiment, said tissue current density induced in the brain of said subject is expressed as a measure of an electric current per unit area of a cross section of the brain of said subject. In a further embodiment of the invention, said induced tissue current density is a measure of a density of flow of a conserved charge and is expressed as a measure of amplitude of said induced tissue current density at said one or more locations in the brain of said subject to an electric conductivity at said predetermined location in the brain. In an embodiment of the invention, said electric conductivity at one or more locations in the brain is a measure of the ability of the brain to conduct electricity and is expressed as Siemens per meter. In an embodiment, said energy density of an electromagnetic field is a measure of an amount of energy stored in or more areas of the brain of said subject per unit volume. In an embodiment of the invention, said energy density is expressed as a measure of an electromagnetic field dissipated per unit volume at said one or more locations in the brain of said subject. In a further embodiment, said electromagnetic field is expressed as a rise time of the transcranial magnetic stimulation pulse applied to the brain in conjunction with said electric field in the brain of said subject in conjunction with said electric conductivity. In an embodiment, said increase in temperature at said one or more locations in the brain of said subject is expressed in degrees Celsius. In an embodiment of the invention, a specific rate of absorption (SAR) at said one or more locations is a measure of the rate at which energy is absorbed by the brain of said subject when exposed to a radio frequency (RF) electromagnetic field.

According to certain embodiments of the invention, said method further comprises the step of: adding together each of said one or more measured responses, so as to determine an accumulated quantity, indicative of a growth of said one or more cumulative effects at each of said one or more locations in said brain.

According to another aspect of certain embodiments of the present invention, there is provided a further method for determining one or more cumulative dose-like quantities of an application of transcranial stimulation to one or more locations in brain of said subject, over a predetermined amount of time; said method comprising the steps of:
  applying one or more transcranial magnetic stimulation pulses to the brain;
  determining a dose of each of said one or more stimulation pulses at each of said one or more locations;
  determining an extent of a response of said brain of said subject within a predetermined amount of time, through the presence or absence of one or more pre-determined external events at each of said one or more locations;
  approximating an accumulation of said doses for at least one, or each, of said one or more locations in the brain of said subject.

Furthermore, there are described herein further embodiments of the invention, particularly well suited for reducing memory consumption, where the method further comprises the steps of:
  determining the spatial difference between one or more predetermined stimulation locations (x) and a corresponding arithmetic mean ($\mu$);
  multiplying said difference by a covariance matrix of a Gaussian function; and
  multiplying said difference by a predetermined weighting variable.

According to certain such embodiments of the invention, the arithmetic mean is a centroid expressed as a three-dimensional vector.

According to another aspect of certain embodiments of the present invention, there is provided a method of representing determined or approximated one or more dose-like effects of application of a transcranial stimulation to brain of a subject to a user, the method comprising the steps of:
  representing said determined or approximated one or more dose-like effects as a scalar map value;
  representing said scalar map value on a visualization of a map of the brain of said subject as a color.

In an embodiment of the invention, a large value in said scalar map value is represented as a bright color on said visualization of the map of the brain and a small value in said scalar map value is represented as a color which is notably dimmer than said bright color on said visualization of the map of the brain.

In certain embodiments of the invention, the visualization of a map of the brain is based on, or comprised of, an image of the subject's brain. In such embodiments of the invention the image of the subject's brain is an MRI, segmented MRI, functional MRI and/or other known brain image.

According to another aspect of certain embodiments of the present invention, there is provided a method of representing determined or approximated one or more dose-like effects of application of a transcranial magnetic stimulation to brain of a subject, to a user, the method comprising the steps of:
  receiving a goal for said representation, where said goal determines information which is essential for said representation and information which is to be removed from said representation as irrelevant; and
  representing said goal as a distinct color on a region of a visualization of a map of the brain of said subject.

In an example embodiment of the invention, said goal is a determination of one or more regions of the brain of said subject that have received a minimum dose of transcranial magnetic stimulation as a treatment. In this embodiment, the method further includes the step of: receiving an input from the user, said input being akin to a transcranial magnetic stimulation of the brain of said subject, so as to progressively color a substantive part of the visualization of the map of the brain of said subject.

In a further example embodiment, said goal is a determination of a maximum dose of said transcranial stimulation. In this embodiment, the method further includes the step of: receiving an input from the user, said input being akin to a transcranial magnetic stimulation of the brain of said subject, said input further including a larger threshold of dosage of stimulation of the brain of said subject, so as to enable the user to stop providing said input when one or more colored spots appear on a region of the visualization of the map of the brain of said subject, which are regarded as sufficiently bright.

In a further embodiment of said invention, a plurality of different distinct colors could be represented on the visualization of the map of the brain of said subject, each of said different distinct colors representing a different goal.

According to certain embodiments of the invention, a direction of a dose of said transcranial magnetic stimulation to brain of a subject is relevant. In an example embodiment, the method may further include the step of: monitoring a dosage so as to avoid doses of a predetermined orientation and magnitude. In a further example embodiment, the method may further include the step of: monitoring a dosage so as to ensure that each part of the brain of said subject obtains a minimum dose in all directions.

According to another aspect of certain embodiments of the present invention there is provided a method of representing determined or approximated one or more dose-like effects of application of a transcranial magnetic stimulation to brain of a subject, to a user, the method comprising the steps of:
  receiving a definition of a vector from the user;
  determining one or more scalar valued endpoints for said definition of the vector;
  visualizing the scalar valued projections as one or more scalar maps on a visualization of a map of the brain of said subject.

In an embodiment of the invention, the step of receiving a definition of a vector from the user includes: directing an arrow using a graphical user interface. In a further embodiment of the invention, the step of receiving a definition of a vector from the user includes: marking two or more endpoints on a three-dimensional view of said visualization of said map of the brain of said subject.

In an example embodiment of the invention, in response to receiving a definition of a vector from the user which relates to one or more vector sums of electric fields or currents, the step of visualizing the scalar endpoints includes the visualization of one or more regions of the brain of said subject where a dose of an electric field or current is directed to an anatomical feature of the brain of said subject which is of interest.

According to another aspect of certain embodiments of the present invention there is provided an apparatus operable to determine one or more cumulative effects of application of one or more transcranial magnetic stimulation pulses to the brain of a subject, said apparatus comprising:
  a stimulator operable to apply said one or more transcranial stimulation pulses the brain of the subject;
  a computer system including a display device;
  a location device for locating the position and alignment of said coil relative to the brain of the subject; and
  a determination unit capable of determining the intensity of stimulation in relative units between individual pulses, within a predetermined amount of time, and issuing to the computer information on the instant of stimulus pulse application, whereby said apparatus is capable of computing from the position and alignment of said coil the presence or absence of one or more external events.

In an embodiment of the invention, said apparatus includes a means of weighting a dose of a transcranial magnetic stimulation pulse train by a repetition rate of said one or more transcranial magnetic stimulation pulses to said brain, so as to determine an effective dose.

According to another aspect of certain embodiments of the present invention there is provided a transitory and/or a non-transitory computer readable medium comprising software for determining one or more cumulative effects of an application of transcranial magnetic stimulation to the brain of a subject, said non-transitory computer readable medium comprising instructions for:
  measuring an extent of a response of said brain of said subject to application of transcranial magnetic stimulation within a predetermined amount of time, through the presence or absence of one or more pre-determined external events; and
  mapping said measured response to a mathematical object having an array of variables, each of said variables representing said measured response of said brain.

According to another aspect of certain embodiments of the present invention there is provided a transitory and/or a non-transitory computer readable medium comprising software for representing to a user said determined or approximated one or more dose-like effects of application of a transcranial magnetic stimulation to a brain of a subject, said non-transitory computer readable medium comprising instructions for:
  visualizing a map of the brain of said subject to whom the transcranial magnetic stimulation is applied;
  representing said determined or approximated one or more dose-like effects as a scalar map value; and
  representing said scalar map value as a color.

DETAILED DESCRIPTION OF EXEMPLARY EMBODIMENTS

Figure 1:
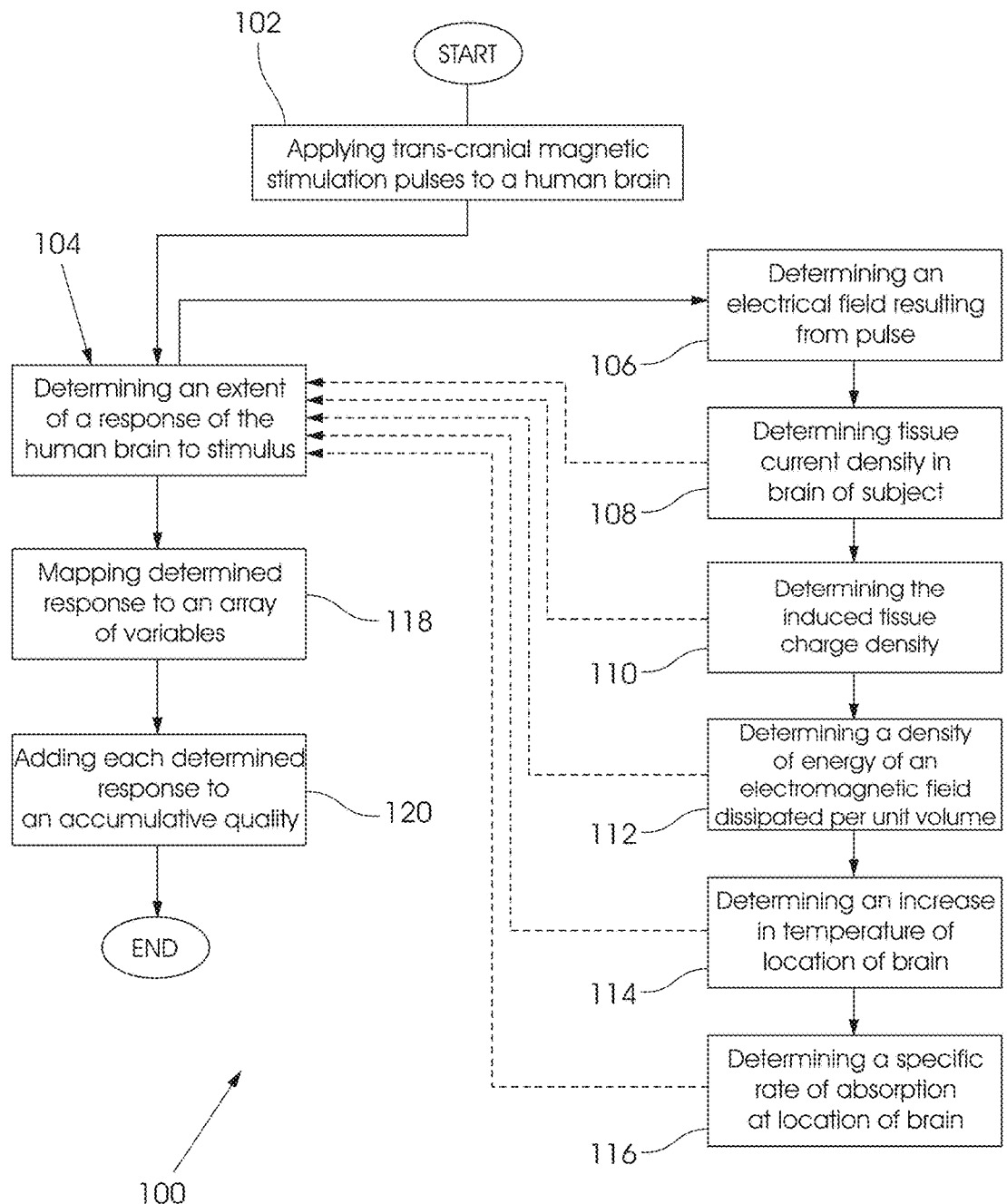
FIG. 1 shows a graphical representation of a method for determining one or more cumulative effects of an application of transcranial magnetic stimulation to the brain of a subject, in accordance with aspects of certain embodiments of the present invention.

Referring to FIG. 1 of the drawings, a method for determining one or more cumulative effects of an application of transcranial magnetic stimulation to the brain of a subject, is generally indicated by reference numeral 100. It is to be appreciated that these cumulative dose-like quantities accumulate in bursts (e.g., of energy, activity, etc.) and decay or dissipate over time.

In terms of an embodiment providing the basic implementation of the method, there is provided a three-dimensional matrix A, the size of which is M×N×K. Each element of the matrix, $A_{i,j,k}$, contains a pair ($\vec{a}_{i,j,k}$,t), where the vector $\vec{a}_{i,j,k}$ has h dimensions and denotes an accumulated dose-like quantity with the timestamp t denoting the time the quantity was last updated.

It will be appreciated that the accumulated quantity is represented by a vector because it is often the case that the quantity has a definite direction, e.g., electric fields and thus cumulative electric fields are directed quantities. Sometimes, however, the size of the vector may be directionless, e.g. accumulated heat.

Each element of the matrix can be attached to a voxel. Each voxel is a basic 3-D element. A sum of voxels make up a blank anatomy of the brain, or region of the brain, of interest. It will be appreciated that when a model of a particular brain is used, e.g. an MRI of a subject's brain, that the voxels are equal to, or approximate, the resolution of the model. However, the volume and dimensions of voxels can be selected or determined to best suit a particular embodiment.

Furthermore, each of the pairs ($\vec{a}_{i,j,k}$,t) is updated in a regular manner. Suppose that the value of the pair is ($\vec{a}_{i,j,k}$,t) prior to an update and ($\vec{a}_{i,j,k}$,t') after the update, where t'>t. The update is based on a sample $\vec{s}_{i,j,k}$ that is associated with the location (i,j,k) and the time t', e.g., the sample may represent a magnetic pulse that, at the instant t', is shot at the location that the element $A_{i,j,k}$ represents.

In particular, a transcranial magnetic stimulation pulse is applied to the brain at block 102 and the dose to the brain of the subject being stimulated with the magnetic stimulation pulse is determined, at block 104.

It is to be appreciated that in determining the direct, macroscopic, dose growth to a human brain, a number of definitions (e.g., (a)-(f) below), derivatives of said definitions and/or combinations of said definitions or derivatives could be provided. Examples of said definitions include:

(a) Expressing the dose as a measure of the electric field $\vec{E}$ surrounding the stimulus, at block 106, expressed in V/m, or the amplitude of the electric field $|\vec{E}|$, at location (i,j,k) caused by the TMS excitation pulse. Methods for calculating the vector field representation of the electric field $\vec{E}$ inside a brain, animal or human, have been presented in, for example, U.S. Pat. No. 6,849,040 as discussed above.

(b) Expressing the dose as a measure of the induced tissue current density $\vec{J}$, at block 108, expressed in A/m$^2$, or the amplitude of the induced tissue current density $|\vec{J}|$, at location (i,j,k), where $\vec{J}=\sigma\vec{E}$ and $\sigma$ is the electric conductivity at location (i,j,k), expressed in S/m. As an example, the electric conductivity of the brain tissue is approximately 0.4 S/m.

(c) Expressing the dose in the human brain to a stimulus as measure of the induced tissue charge density Q, at block 110, expressed in C/m$^2$, at location (i,j,k), where $Q=t_r|\vec{J}|$ and $t_r$ is the rise time of the TMS excitation pulse.

(d) Expressing the dose as a measure of the energy density of the electromagnetic field W, at block 112, dissipated per unit volume at location (i,j,k), expressed in J/m$^3$, where $W=t_r\sigma|\vec{E}|^2$, $t_r$ is the rise time of the transcranial magnetic stimulation pulse and $\sigma$ is the electric conductivity.

(e) The extent of the dose in the human brain to a stimulus can be expressed as measure of the temperature increase Q at location (i,j,k), expressed in ° C., at block 114.

(f) The extent of the dose in the human brain to a stimulus can be expressed as a measure of the Specific Absorption Rate SAR, expressed in W/kg, at location (i,j,k), where $$SAR = \frac{\sigma|\vec{E}|^2}{\rho}$$

and $\rho$ is the density at location (i,j,k) expressed in J/m$^3$, at block 116.

Furthermore, either alone or in addition to direct dose calculation there may be one or more secondary considerations and/or inputs for determining the dose from stimulation. For example, the estimated change in neuron membrane potential can be considered.

Neighborhood scatter can also be taken in to account. Scatter can be a general estimated scatter or it can be dependent upon brain anatomy. For instance, when a segmented MRI is utilized it is possible to identify different types of tissue and matter within the brain. As different types of tissue and matter react differently to stimulation, and scatter, then the characteristics of the particular tissue or matter can be considered. Furthermore, the boundaries between different types of tissue and matter have a distinct effect on stimulation dilution and particularly on scatter.

In certain embodiments, each voxel or groups of voxels are associated with their corresponding known, estimated or inferred tissue/matter type. These groups of voxels can create functional neighborhoods. For example, there can be a group of voxels which represent spinal fluid which boarders a group of voxels which represent grey matter. When a specific area of grey matter is stimulated then the neighboring grey matter within the functional neighborhood will experience a certain scatter effect which can be taken in to consideration in the cumulated dose for that area. The neighboring spinal fluid which boarders that area will have a different scatter effect based on the difference in matter and/or boarder conditions. Therefore, scatter can more accurately be estimated and taken in to consideration. Other types of anatomical information which has an effect on stimulation distribution, scatter, accumulation and/or decay can be similarly incorporated in secondary considerations.

The results of one or more of the abovementioned definitions, derivatives thereof and/or secondary considerations can then be mapped as an array of variables in the matrix A, at block 118.

In order to determine the growth (g) function, the abovementioned determined dose is then compiled so as to determine an accumulated quality, at block 120:

In this regard, a general update rule is $$(\vec{a}_{i,j,k},t')=(d(g(\vec{a}_{i,j,k},\vec{s}_{i,j,k},t'),t,t')t'), \quad (1)$$

where g: $\mathbb{R}^h \times \mathbb{R}^h \times \mathbb{R} \to \mathbb{R}^h$ maps an accumulated result, a sample, and a timestamp into a new accumulated result, and where d: $\mathbb{R}^h \times \mathbb{R} \times \mathbb{R} \to \mathbb{R}^h$ maps an accumulated result and two timestamps into a new accumulated result. Intuitively, g represents growth and d represents decay. The growth of the accumulated quantity depends on the determination of instantaneous external events, i.e., the samples. Decay occurs in the absence of external events, and uses the time differential between t and t' to undo some of the growth.

In practice, the functions g and d may be quite simple, for example:

$$g(\vec{a}_{i,j,k},\vec{s}_{i,j,k},t')=\vec{a}_{i,j,k}+\vec{s}_{i,j,k} \quad \text{(linear growth)},$$

$$d(\vec{a}_{i,j,k},t,t')=\vec{a}_{i,j,k}-\beta(t'-t) \quad \text{(linear decay)},$$

$$d(\vec{a}_{i,j,k},t,t')=\vec{a}_{i,j,k}\beta^{-\alpha(t'-t)} \quad \text{(exponential decay)}.$$

The specific type of growth and/or decay functions g and d may be selected, e.g., according to the accumulated quantity. For example, exponential decay occurs in a wide variety of situations, and most of these fall into the domain of the natural sciences. For example, if an object at one temperature is exposed to a medium of another temperature, the temperature difference between the object and the medium follows exponential decay provided that certain conditions are met. It is to be appreciated that the computations provided above can be executed in parallel for each $A_{i,j,k}$ as long as g and d are formulated strictly as above, i.e., growth and decay are completely local in the sense that the neighbors $A_{.,.,.}$ of the element $A_{i,j,k}$ do not affect the update of $A_{i,j,k}$. This result holds regardless of the specific choice of g and d, e.g., linear, exponential, or other.

In this regard, it is to be appreciated that in a further embodiment of the invention, neighbors could be made to affect the computation, e.g., low-pass filtering over the neighborhood might be used in g to reduce noise ins.

Using the matrix A, the above computations may require large amounts of memory. Supposing that each $\vec{a}_{i,j,k}$ takes B bytes of memory and each timestamp takes 4 bytes, each $(\vec{a}_{i,j,k},t)$ takes B+4 bytes, and the matrix A takes M×N×K×(B+4) bytes. Simple directionless quantities accumulating over MRI images can require 256×256×256×(4+4)=128 megabytes. More complex, detailed quantities over similar images can require on the order of 256×256×256×(24+4)= 448 megabytes.

Because the matrix A, implemented in a basic manner, may require a substantial amount of memory there is described herein methods for decreasing memory consumption. If, in the matrix A, the values of the vectors $\vec{a}_{i,j,k}$ (of the value pairs $(\vec{a}_{i,j,k},t)$ contained by the elements $A_{i,j,k}$) change smoothly over space (i.e., over i,j,k), it is possible to use radial basis functions to create a sufficiently accurate and compact approximation of A.

Figure 2:
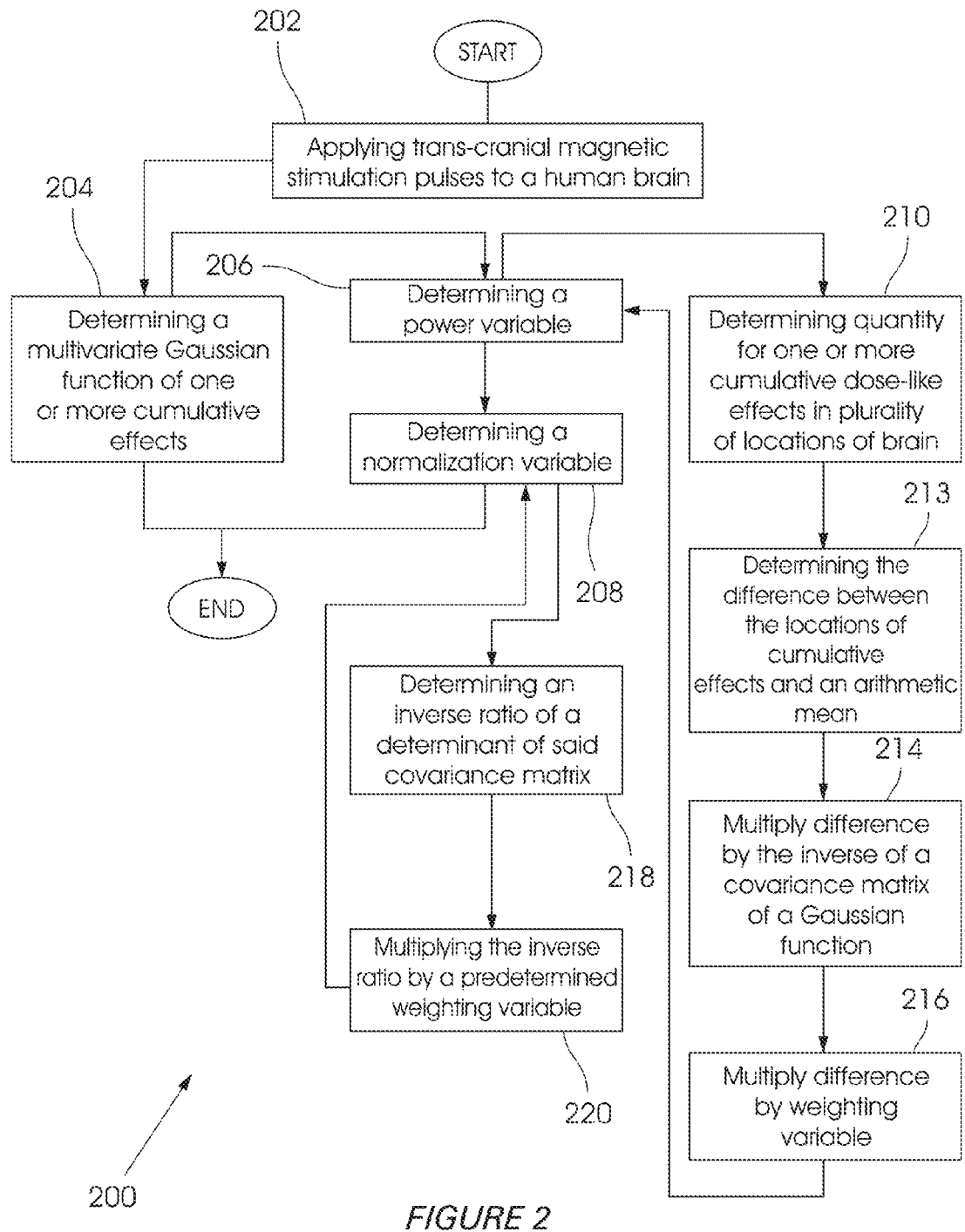
FIG. 2 shows a graphical representation of an embodiment of a method for determining one or more cumulative effects of an application of transcranial magnetic stimulation to the brain of a subject, in accordance with aspects of certain embodiments of the present invention.

With reference to FIG. 2, an exemplary method for determining a kernel for a relevant approximation of A is generally indicated by reference numeral 200. The method of FIG. 2 is particularly well suited when the values of $(\vec{a}_{i,j,k})$ change smoothly over space and/or when there is a constraint on memory resources.

In accordance with the method 200, a transcranial magnetic stimulation pulse is applied to the brain of a subject, at block 202. A basic function, i.e. a kernel, is selected to be used in the approximation. The kernel can be a chosen from a variety of basic functions, most often exponential functions. In terms of the present embodiment a multivariate Gaussian function of the cumulative effects of the stimulation pulse on the human brain is then determined, at block 204, and utilized as the kernel. If a kernel is not determined from an available set in step 204 then the method of the present embodiment continues through steps 206-220 to determine an appropriate multivariate Gaussian function.

In terms of a Gaussian function there is provided a power variable and a normalization variable which are to be determined at block 206 and 208. In so far as a determination of the power variable of the Gaussian function, at block 206, is concerned, growths, decays and/or cumulative quantities of one or more cumulative dose-like effects are determined for each stimulated part of the brain, at block 210. In other words, a determination of a dose quantity for locations, $\vec{x}$, takes place.

At block 213, the spatial difference, e.g. in the three-dimensional space, between the abovementioned dose location and an arithmetic mean is determined. In other words, a determination of the difference between locations $\vec{x}$ and the corresponding centroid $\vec{\mu}$ location, said centroid being a three-dimensional vector $[i,j,k]^T$, takes place. In the h-dimensional case:

$$(\vec{x};\vec{\mu},\{\vec{C}_m\}_{m=1}^h)=[w(\vec{x};\vec{\mu},\vec{C}_1),\ldots,w(\vec{x};\vec{\mu},\vec{C}_h)]^T.$$

At block 214, the spatial difference between the abovementioned location and the arithmetic mean is multiplied by the inverse of a covariance matrix of the Gaussian function, also known as C, i.e. $C^{-1}$.

Further to the above, the abovementioned difference is then further multiplied by a weighting variable. In particular, the weighting variable in the present embodiment is $-\frac{1}{2}$.

In determining the normalization variable, at block 208 an inverse ratio of a determinant of the covariance matrix is determined, i.e. |C|, at block 218. Furthermore, this ratio is multiplied by a predetermined weighting variable, at block 220. In particular, a weighting variable of $2\pi^{3/2}$ is required.

In terms of the power variable and the normalization variable determined above, for the following approximation method of A (as indicated above which is particularly useful when A consumes plenty of memory and the values of the vectors $\vec{a}_{i,j,k}$ change smoothly over space) the kernel is provided:

$$w(\vec{x};\vec{\mu},C) = \frac{1}{2\pi^{3/2}|C|^{1/2}} e^{-\frac{1}{2}(\vec{x}-\vec{\mu})^T C^{-1}(\vec{x}-\vec{\mu})}, \quad (2)$$

Figure 3:
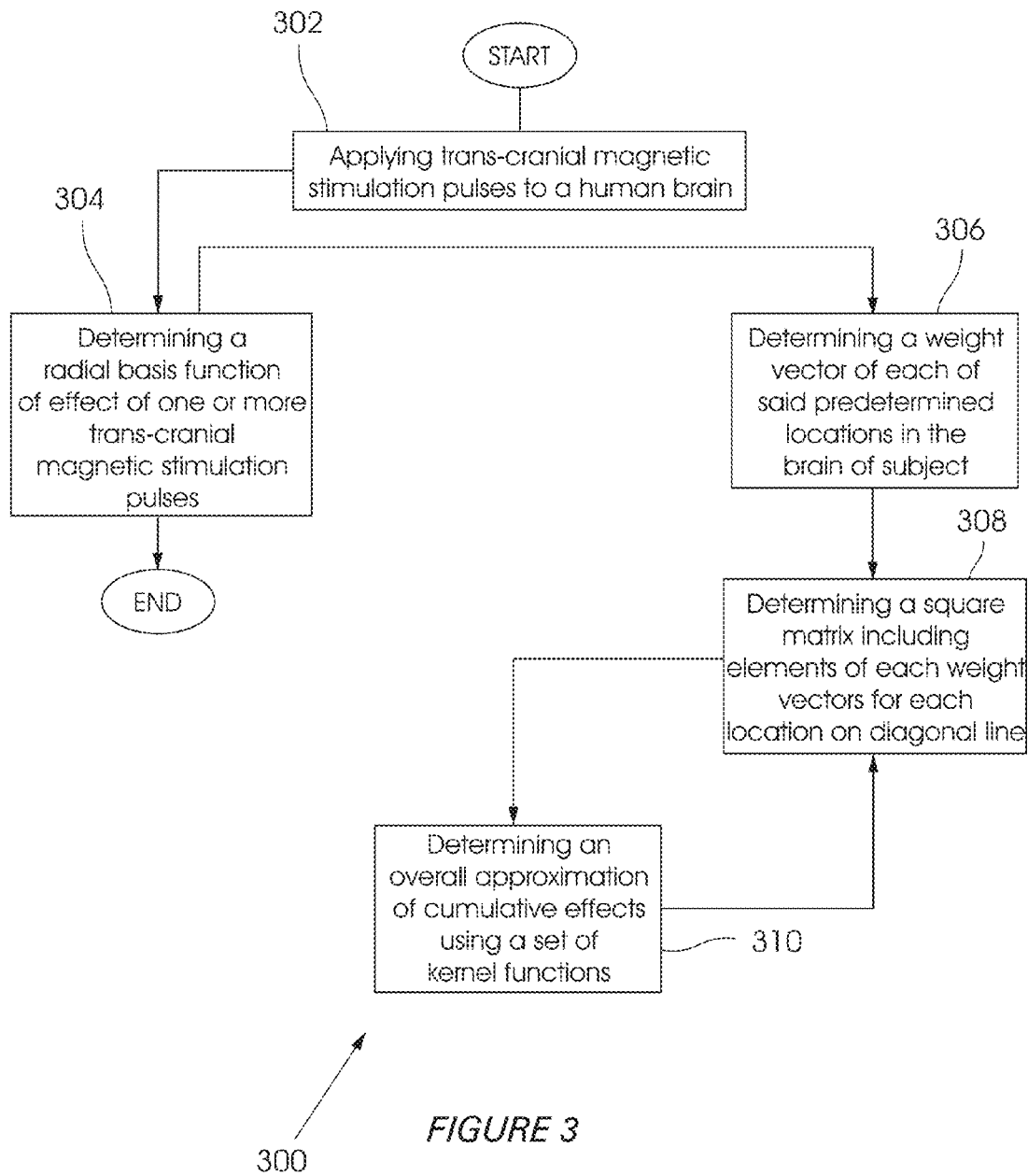
FIG. 3 shows a graphical representation of an embodiment of a method of determining one or more cumulative effects of an application of transcranial magnetic stimulation to the brain of a subject, in accordance with aspects of certain embodiments of the present invention.

With reference to FIG. 3, a continuation of the method for determining an approximation of A for one or more cumulative effects of an application of transcranial magnetic stimulation to the brain of a subject, is generally indicated by reference numeral 300.

The method 300 includes applying a transcranial magnetic stimulation pulse to the brain, at block 302. As the function A is to be approximated in the present embodiment, a radial basis function of the effects of one more transcranial stimulation pulses is determined at block 304, an expanded explanation being shown previously with regards to FIG. 2. The method includes determining a weight vector of each of the predetermined locations in the brain of the subject at block 306 and determining a square matrix including elements of each weight vector of each location, on a diagonal line in the matrix, at block 308.

As regards the determination of a square matrix, as set out in block 308, an overall approximation of the cumulative effects, using a set of kernel functions, is determined at step 310.

The overall approximation for a data-point $\vec{x}=[i,j,k]^T$ using a set of kernels Z is calculated a:

$$rbf(i,j,k;Z)=\Sigma_{l=1}^{|Z|} \text{diag}(\vec{a}_l)\vec{w}_l([i,j,k]^T;\vec{\mu}_l,C_l), \quad (4)$$

where $\vec{a}_l$ is the weight vector assigned to the lth kernel $\vec{w}_l$, and $\text{diag}(\vec{a}_l)$ is a square matrix with the elements of $\vec{a}_l$ on the main diagonal.

The number size of the set of kernels Z can be freely selected or predetermined. The size of the set may be equal to, greater than or less than the total number of locations x. When the number of kernels is less than the total number of locations x then a single kernel can be representative of an area, i.e. a plurality of individual data points $\vec{x}$.

In a further embodiment of the invention, the cumulative dose-like effects can be computed as a functional module, operable to be executed in a conventional processor of a computer system, the functional module being in the example form of a computer program.

In terms of said embodiment, the algorithm sought to be implemented through the functional module may include some or all of the following distinctive characteristics:

an online-algorithm and/or a batch-algorithm, i.e., the approximation is built piece-by-piece in a serial fashion.

a constant number of kernels due to the elimination technique of removing the oldest kernel during each iteration.

an elimination technique (a heuristic) based on the assumption that the decay function in (1) tends to make the oldest kernel(s) irrelevant if Z is large enough considering the rate of decay.

An example is provided:

Let Z be some initial set of radial basis kernels each centered at some i,j,k.

Let t:=0 be an initial timestamp.

For each new event $(\vec{s}, t')$ in the order of occurrence:

```
For each (i, j, k) ∈ {1, ... , M} × {1, ... , N} × {1, ... , K}:
    x⃗ = rbf (i, j, k; Z)
    x⃗' = d (g (x⃗, s⃗_{i,j,k}, t'), t, t')
    if dif f (x⃗, x⃗') < T:
        do nothing
    else:
        Remove the oldest kernel o: Z := Z − {o}.
        Let w be a new kernel such that:
            dif f (rbf (i, j, k; Z ∪ {w}), x⃗') < T.
        Update Z := Z ∪ {w}.
Update t := t'.
```

Above, the oldest kernel is simply one that has been in Z for the longest, i.e., no other kernel in Z has been used to process more events $(\vec{s}, t')$. In case of ties, the choice may be randomized or selected based on any number of applicable means.

It will be appreciated that in terms of the methods exemplified above, we have a map function f that produces map values, e.g., $f(i,j,k)=A_{i,j,k}$ or $f(i,j,k)=rbf(i,j,k;Z)$. In this regard it will be appreciated that the map values may be scalars or vectors.

The determined map values can then be communicated to the user of a system in a useful manner. In this regard two types of visualizations may be provided individually or in combination: termed a general visualization and a goal-based visualization.

In particular, with reference to the abovementioned two forms of representation, the general visualization presents information as it is, e.g. in a rich form. Within the goal-based visualization, the goal determines which information is presented as essential and which is treated, e.g. removed, as irrelevant to the goal. It will be appreciated that the general visualization form is particularly useful for exploratory studies whereas the goal-based visualization form is particularly useful for more focused clinical work, such as verifying the delivered dose.

Figure 4:
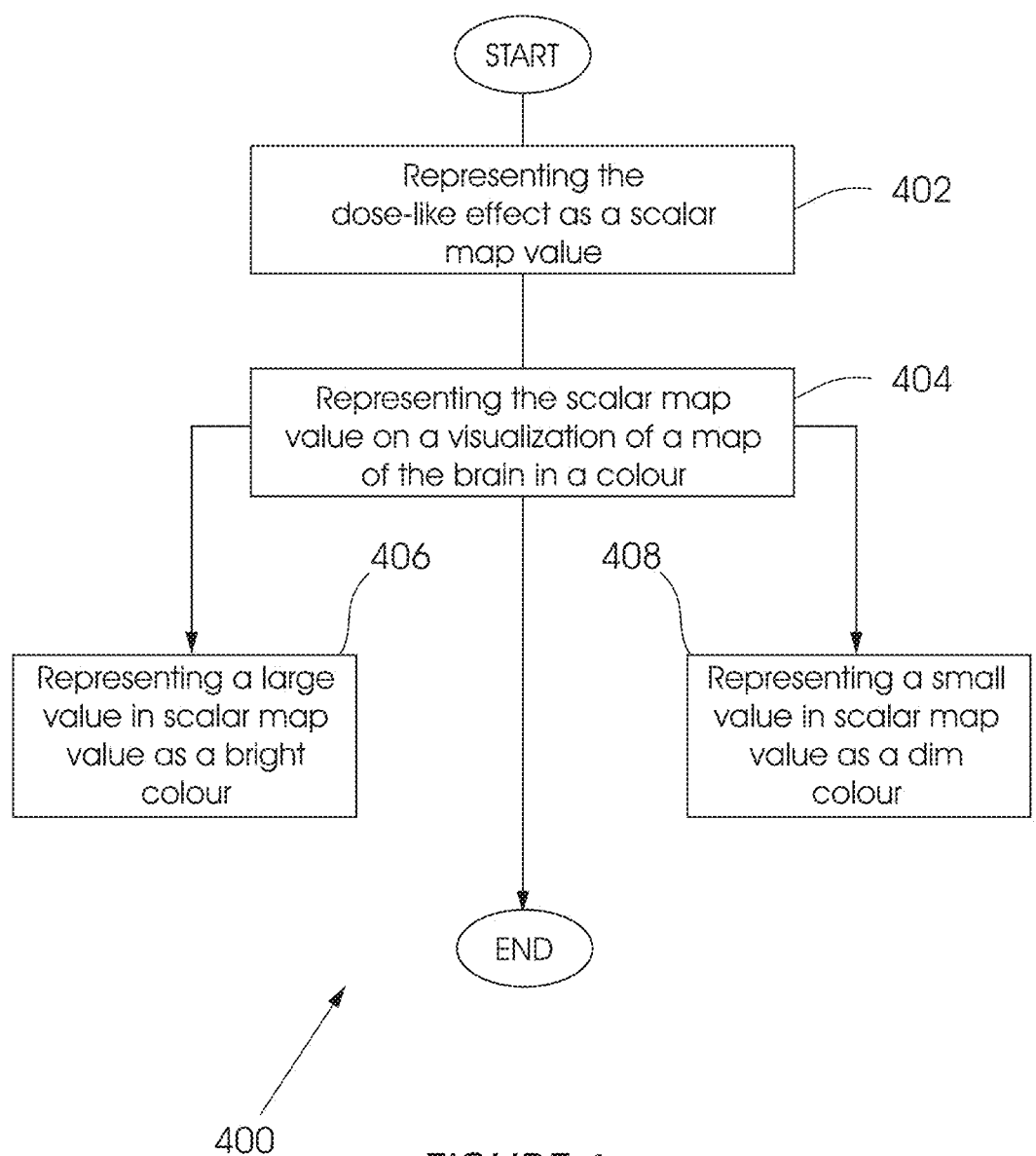
FIG. 4 shows a graphical representation of a method of representing the determined or approximated one or more dose-like effects of application of a transcranial magnetic stimulation to brain of a subject, to a user.
Figure 5:
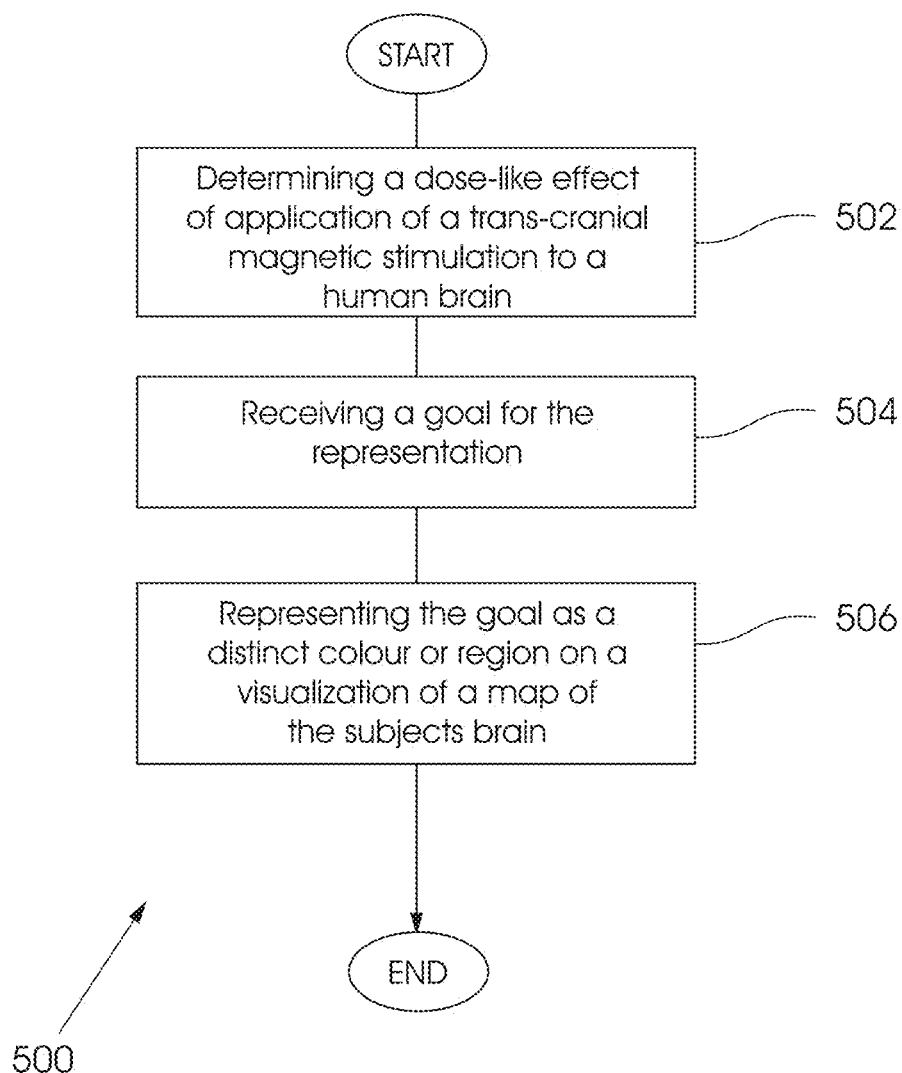
FIG. 5 shows a graphical representation of a method of representing the determined or approximated one or more dose-like effects of application of a transcranial magnetic stimulation to brain of a subject, to a user, in accordance with aspects of certain embodiments of the present invention.

With reference to FIG. 4, a method of representing the determined or approximated one or more dose-like effects of application of a transcranial magnetic stimulation to brain of a subject is exemplified. In terms of this method, a scalar map is provided representing the determined cumulative dose-like effects as a scalar value, at block 402. The scalar map value is then represented as a map value in the form of a bright color on a visualization map of the brain of the subject subjected to stimulation pulses, at block 404. In particular, a color is painted on a visualization surface provided by navigated brain stimulation software (such as Nexstim NBS), e.g., as exemplified as a peeling view of the brain or a cutting (sector) view of the brain.

More particularly, a large value in a scalar map value is indicated as bright color, as indicated at block 406 and a small value in a scalar map value is indicated as a dim color, as indicated at block 408. It will be appreciated that a separate visual slider may be used to alter the transparency of the visualization surface so that the user may focus either on the map values or the underlying anatomy shown simultaneously by the navigated brain stimulation software.

Though colors offer a particularly good visual representation, different gray values, colored and/or non-colored outlines, references (e.g. numbers, letters, characters, etc.) and the like may be used in conjunction with or in place of different colors.

In terms of another aspect of certain embodiments of the present invention, a further method of representing the determined or approximated one or more dose-like effects of application of a transcranial magnetic stimulation to brain of a subject is generally indicated by reference numeral 500.

According to a first step of the method, a dose-like effect of application of a transcranial magnetic stimulation to a human brain is determined, at block 502. A user can then specify a goal for the representation, a goal can be expressed as a function $G(i,j,k,f(i,j,k)):\mathbb{R}^4 \to \{0,1\}$, at block 504. In response to receiving a goal, the method comprises transforming a map position and a map value in that position into a zero if the position and value do not satisfy the goal, and to a one if the position and value satisfy the goal.

A simple but useful goal would be one that is satisfied for a voxel i,j,k whenever $f(i,j,k) > 20$ V/m. In other words, a goal-based visualization in its simplest form could use an indicator, e.g. a bright color, to paint those parts of the brain that have received the minimum dose for treatment, as exemplified at block 506. In this manner, the user could then keep stimulating until all relevant parts of the brain get painted by the bright color. It will be appreciated that in terms of this method, if a user wanted to define and monitor a maximum dose, then a larger threshold could be specified and the user could stop stimulating a brain area immediately after bright spots start to appear on that area. It will further be appreciated that both maximum and minimum doses can easily be monitored at the same time by using just two color codes for goals (recall that in goal-based visualization irrelevant information such as extensive color-maps and unnecessary colors are not visualized; each specific goal has a distinct color that appears on top of the regions that satisfy that goal).

It will be appreciated that, with reference to the abovementioned method, it could be appropriate to use a color map such that bright colors indicate large map values and dim colors indicate small values. It will be appreciated that because the map portrayed through the abovementioned method contains vectors, to design a color map becomes more difficult.

Figure 6:
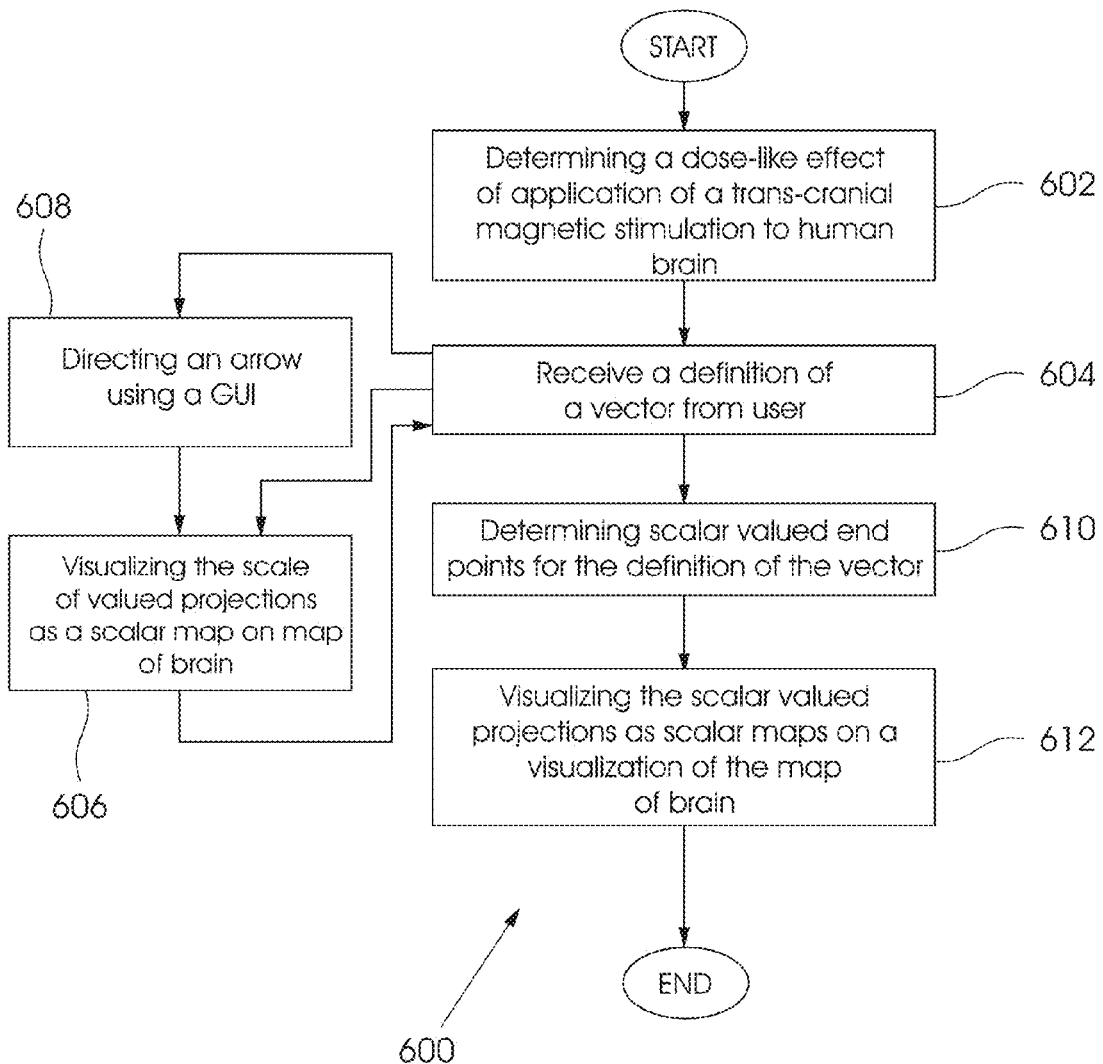
FIG. 6 shows a graphical representation of a method of representing the determined or approximated one or more dose-like effects of application of a transcranial magnetic stimulation to brain of a subject, to a user in accordance with aspects of certain embodiments of the present invention.

A proposed solution to the abovementioned problem is based on a dimensionality reduction of the map. In this regard, with reference to FIG. 6, a further method of representing the determined or approximated one or more dose-like effects of application of a transcranial magnetic stimulation to brain of a subject, which uses dimensionality reduction is generally indicated as reference numeral 600.

Firstly, the dose-like effects of the application of a transcranial magnetic stimulation is determined, at block 602. At block 604, the user defines a vector, e.g., by directing an arrow using the GUI, at block 606, or marking two endpoints on the three-dimensional view of the navigated brain stimulation software, at block 608. Secondly, a functional module in the computer system is used to determine the scalar valued projections $p_{\vec{f},\vec{w}}(i,j,k) = \vec{w}^T \vec{f}(i,j,k)$ for the definition of the vector provided, at block 610. Finally, the scalar valued projections are visualized as scalar maps were visualized on a map of the brain, at block 612.

In an example embodiment of this method, the map of the brain can contain vector sums of electric fields or currents. In this embodiment, the user might want to visualize the regions of the brain where the dose of fields or currents were directed toward an anatomical feature of interest.

It will be appreciated that in terms of a further embodiment more complex goals can be expressed and colored on the visualization surfaces produced by the functional modules of the computer system, in the example form of the navigated brain stimulation computer program.

For example, with reference to the abovementioned monitoring example, the system can be extended and refined so that the directions of the doses matter. In this manner, a user could use monitoring to avoid doses of some specific orientation and magnitude or one could try to ensure that each part of the brain gets the minimum dose in all orientations.

In terms of another embodiment of the invention, the results of the abovementioned visualization methods can be saved in, or converted to DICOM format (DICOM Structured Report—type [5], possibly with RT-extensions) to ensure that the results are immediately usable with commercial DICOM-enabled workstations.

Figure 7:
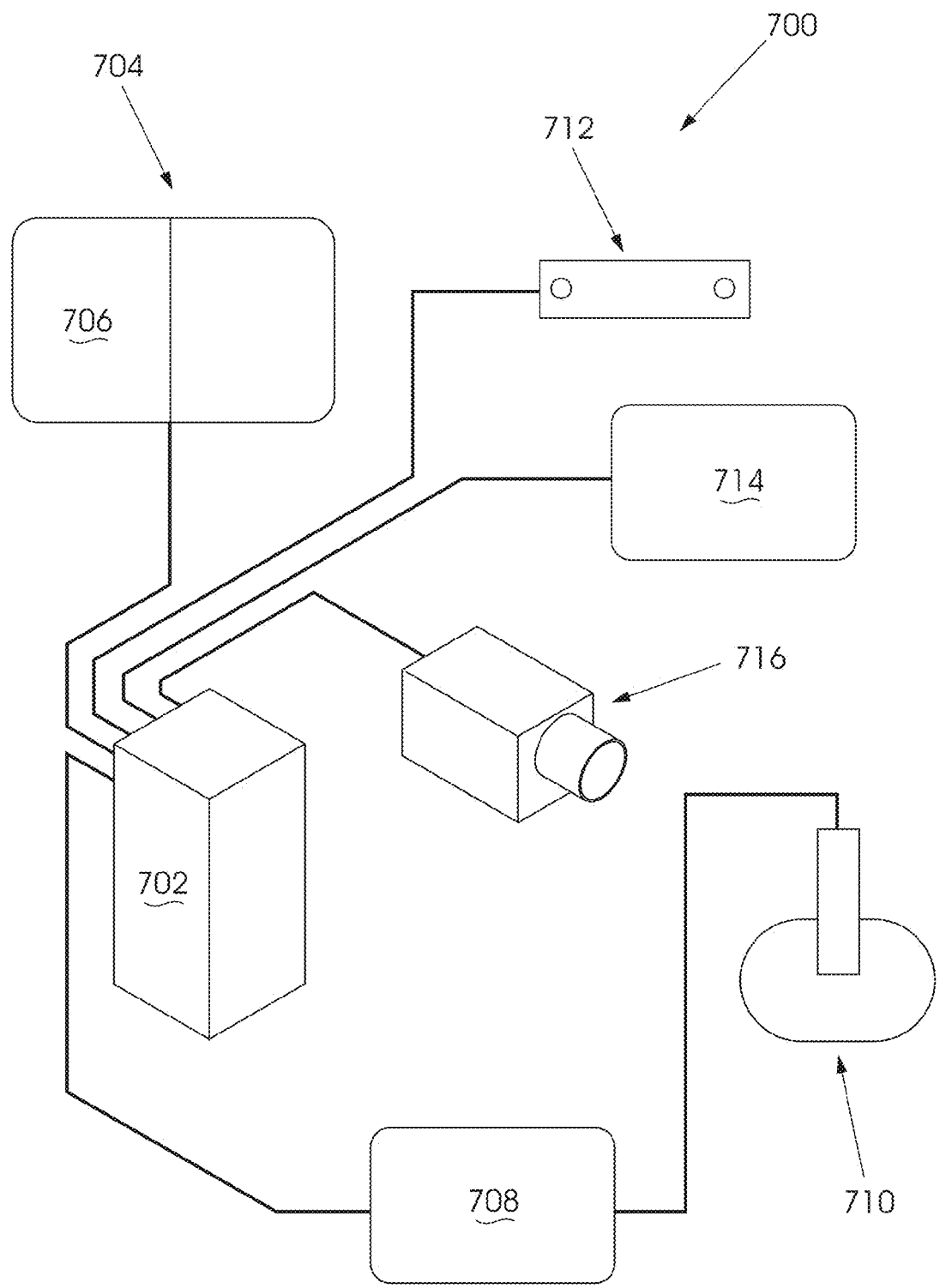
FIG. 7 shows a graphical representation of a system in terms of which the methods exemplified in either one of FIGS. 1 to 6 can be implemented.

With reference to FIG. 7, a system 700 in terms of which the methods exemplified with reference to FIGS. 1 to 6 can be implemented is illustrated. In particular, Navigated Brain Stimulation (NBS) software insures the stimulation of specific locations of a subject's brain. In order to map a portion of a subject's brain functions the specific location of any stimulation should be accurately known. Therefore, NBS utilizes a tracking system such as 712 and tracking software in order to know the location of the stimulating device 710, or at least the relative location of the stimulating device 710 in relation to a subjects head and/or brain.

Several methods are known in which the location of a stimulating device 710 can be determined and several are described in more detail at least in US 2008/058582, "Transcranial magnetic stimulation induction coil device with attachment portion for receiving tracking device" which is herein incorporated by reference. At least some of these methods include tracking markers on or attached to the stimulating device 710. Additionally, markers can be attached to one or more locations on a subject's head, as described for example in US 2005/075560, "Stereotactic frame and method for supporting a stereotactic frame" which is herein incorporated by reference.

When markers are used in the tracking of the stimulation device 710 and/or the subject's head, a tracking system 712 is utilized which is capable of recognizing at least some or all of the markers. For example, if the markers used are capable of reflecting infrared light, then the tracking system 712 is an infrared tracking system or at least incorporates an infrared tracking system. Such an infrared tracking system can include one, two or more infrared tracking devices, such as infrared cameras, which are able to spatially locate the tracked objects in a three-dimensional environment.

Other methods of tracking the stimulation device 710 and the subject's head are described in the aforementioned publications. In addition, one of ordinary skill in the art will recognize methods of tracking objects which can be utilized with the present system without departing from the scope of the present invention. Such methods include, for example, a tracking system 712 which includes at least one camera 716 capable of capturing and/or recording visible light and tracking visual markers, light reflective markers, LEDs and/or objects themselves.

In certain embodiments, there is a single tracking system 712 which tracks both the stimulation device 710, the subject's head and any other desired tracked object(s). In certain other embodiments, more than one tracking system 712 is utilized for tracking a certain object or one or more objects have their own tracking systems (not shown). Information from the tracking system(s) is then sent to NBS navigation software.

Tracking data from the tracking system 712 is input to NBS navigation software which is then able to display NBS information on a NBS portion 706 of an operator display 704. The NBS display 706 is capable of showing an operator the location of the stimulation device 110 in relation to the subjects head. Additionally, the NBS display 706 can utilize at least one head model to show actual stimulation locations on a subject's brain and/or projected stimulation locations based on the location of the stimulation device 710. Examples of head models are the subjects CT, the subjects MRI, a similar subjects CT or MRI or a standard head. U.S. Pat. No. 7,720,519, "Method for three-dimensional modeling of the skull and internal structures thereof", herein incorporated by reference, discloses several methods for selecting and utilizing head models in NBS navigation.

NBS navigation software is capable of showing the stimulating tools as rigid objects, and showing predicted brain activation by modeling in real-time or off-line the electromagnetic properties of the coil and the patient head. These models can be obtained by applying known bioelectromagnetic methods, such as spherical modeling, boundary element method or finite element method. Some additional functionality is described in more detail with regards to example embodiments and also in U.S. application Ser. No. 11/853,232, "A method for visualizing electric fields on the human cortex for the purpose of navigated brain stimulation", now U.S. Pat. No. 9,101,751, and Ser. No. 11/853,256, "Improved accuracy of navigated brain stimulation by online or offline corrections to co-registration", now U.S. Pat. No. 7,925,066, which are herein incorporated by reference. Furthermore, those of ordinary skill in the art will recognize modifications to the NBS navigation software and tracking system described herein which does not depart from the scope of the present invention.

It will be appreciated that, in addition to the above, the invention has further short-term applications in rTMS. In this regard it is possible to predict that the invention has further commercial potential related to treatment processes, including applications which are localized, or memory-based, i.e. effects have "memory" in the sense that they build up or decay over time.

Furthermore, it will be appreciated that there are further embodiments of the invention, where there is provided another method for approximating one or more cumulative effects, over a predetermined amount of time, of an application of transcranial magnetic stimulation to one or more predetermined locations in the brain of a subject; said method comprising the steps of:
  applying one or more than one transcranial magnetic stimulation pulses to the brain; and
  determining a radial basis function of the effect of said one or more transcranial magnetic stimulation pulse to the brain for each of said one or more locations in a brain of said subject.

In an embodiment of the invention, determining said radial basis function includes the steps of:
  determining a weight vector for one or more, or each, of one or more kernels;
  determining a square matrix including the elements of each of said weight vectors determined for each of said kernels on a diagonal line of said square matrix.

In an embodiment of the invention, determining said square matrix includes the following steps:
  determining an arithmetic mean of said growth of said cumulative effects; and
  determining a Covariance matrix of a multivariate Gaussian of said one or more cumulative effects.

Furthermore, there is described herein a set of clauses exemplary of particular embodiments. Clause 1, a method of determining one or more cumulative effects of an application of transcranial stimulation to at least one location in a brain of a subject, said method comprising the steps of, applying at least one transcranial stimulation pulse to said at least one location in said brain, determining a cumulative dose over time from said at least one transcranial stimulation pulse for one or more affected locations in the brain, mapping said determination to a mathematical object having an array of variables, each of said variables representing said determination at affected locations in the brain.

Clause 2, a method according to clause 1, wherein determining a cumulative dose over time includes a decay component. Clause 3, a method according to clause 1 or 2, wherein said transcranial stimulation is in the form of magnetic stimulation. Clause 4, a method according to any of the preceding clauses, wherein said transcranial stimulation is in the form of high frequency stimulation, ultra-sound stimulation and/or optical stimulation.

Clause 5, a method according to any of the preceding clauses, wherein said method further comprises the step of: determining an accumulated quantity, indicative of a growth and decay of said one or more cumulative effects at each affected location in said brain.

Clause 6, a method according to any of the preceding clauses, wherein the determined cumulative dose is based at least in part on: an electric field resulting from the transcranial stimulation pulse, a tissue current density induced in a brain of said subject, a density of energy of an electromagnetic field dissipated per unit volume at said one or more locations in the brain of said subject, an increase in temperature at said one or more locations, a physical response of a subject, a verbal response of a subject, a cognitive response of a subject, and/or a specific rate of absorption at said one or more locations or combination thereof.

Clause 7, a method for determining one or more cumulative dose-like quantities of an application of transcranial stimulation to one or more locations in brain of said subject, over a predetermined amount of time; said method comprising the steps of: applying multiple transcranial magnetic stimulation pulses to the brain; determining a dose of each of said stimulation pulses at each of said one or more locations; measuring a physical response of said subject within a predetermined amount of time, through the presence or absence of one or more pre-determined external events at each of said one or more locations; approximating an accumulation of said response of said brain for each of said one or more locations in the brain of said subject based at least upon the determined dose and a decay factor.

Clause 8, a method according to clause 7, further comprising the steps of: representing said approximated one or more dose-like effects as a scalar map value; and representing said scalar map value on a visualization of a map of the brain of said subject as one or more a colors and/or outlines. Clause 9, a method according to clause 8, wherein a large value in said scalar map value is represented as a bright colour on said visualization of the map of the brain and a small value in said scalar map value is represented as a colour which is notably dimmer than said bright colour on said visualization of the map of the brain. Clause 10, a method according to any of the preceding clauses, further comprising the steps of: receiving a goal, where said goal determines information which is essential and information which is to be removed as irrelevant; and representing said goal with a distinct indication, such as a distinct color, on a region of a visualization of a map of the brain of said subject.

Clause 11, a method of representing determined or approximated one or more dose-like effects of application of a transcranial magnetic stimulation to brain of a subject, to a user, the method comprising the steps of: receiving a definition of a vector from the user; determining one or more scalar valued endpoints for said definition of the vector; visualizing the scalar valued projections as one or more scalar maps on a visualization of a map of the brain of said subject.

Clause 12, a method according to clause 11, wherein in response to receiving a definition of a vector from the user which relates to one or more vector sums of electric fields or currents, the step of visualizing the scalar endpoints includes the visualization of one or more regions of the brain of said subject where a dose of an electric field or current is directed to an anatomical feature of the brain of said subject which is of interest.

Clause 13, an apparatus 700 operable to determine one or more cumulative effects of application of one or more transcranial magnetic stimulation pulses to the brain of a subject, said apparatus comprising: a stimulator 708 operable to apply said one or more transcranial stimulation pulses the brain of the subject; a computer system 702 including a display device 704, 706, 708, 714; a location means 712 for locating the position and alignment of said coil 710 relative to the head and/or brain of the subject; a measurement means 716 for determining the presence or absence of one or more external events in response to stimulation; and a means of weighting a dose of a transcranial magnetic stimulation pulse train by a repetition rate of said one or more transcranial magnetic stimulation pulses to said brain, so as to determine an effective dose. Clause 14, an apparatus according to clause 13 wherein the determined effective does includes a decay component.

The examples and embodiments described herein are meant to help illustrate the present invention and are not meant as limiting examples. Numerous variations and combinations of elements from the specific embodiments and examples disclosed herein can be achieved by those of ordinary skill in the art without departing from the scope of the present invention. Furthermore, modifications and techniques known to those of ordinary skill in the art but not disclosed herein may be made without departing from the scope of the invention.

The invention claimed is:

1. A method of determining one or more cumulative effects of an application of navigated transcranial magnetic stimulation to at least one location in a brain, said method comprising computer implemented steps of:
   determining a three dimensional area of a stimulation dose induced by a navigated transcranial magnetic stimulation pulse from a coil device,
   determining a growth function of the stimulation dose in at least one location of the brain, wherein the growth function is derived at least partially according to a known, inferred or estimated tissue type of the at least one location of the brain,
   determining a decay function of the stimulation dose in said at least one location of the brain, wherein the decay function is at least partially derived from a period of elapsed time after the stimulation dose,
   calculating a cumulative stimulation dose for said at least one location of the brain based on the growth function and the decay function at one or more points in time, and
   administering the navigated transcranial magnetic stimulation to the brain, wherein the administering is based at least partially on the calculated cumulative stimulation dose.

2. A method according to claim 1, further comprising the step of determining a relative location and orientation of the determined three dimensional area of the stimulation dose in relation to at least one predetermined anatomical marker in the brain.

3. A method according to claim 1, further comprising the step of determining a relative location and orientation of the determined three dimensional area of the stimulation dose within a region of the brain which has been at least partially mapped using navigated transcranial magnetic stimulation.

4. A method in accordance with claim 1, wherein the calculated cumulative stimulation dose is calculated for each location within the specific area of interest of the brain or for an entire brain.

5. A method in accordance with claim 4, wherein cumulative stimulation doses for a plurality of locations are timestamped and aggregated in a matrix.

6. A method in accordance with claim 1, wherein the cumulative stimulation dose for one or more locations is updated based on an additional growth function and/or the expiration of a period of time.

7. A method in accordance with claim 1, wherein the growth function, decay function and/or cumulative stimulation dose for each location contains a timestamp.

8. A method in accordance with claim 1, wherein the at least one cumulative stimulation dose is displayed in a visual format on a model of the brain for a corresponding location at a given time.

9. A method in accordance with claim 8, wherein the model of a brain is a Magnetic Resonance Image (MRI).

10. A method in accordance with claim 8, wherein a size of each location is approximately a size of resolution for the model of the brain.

11. A method of determining one or more cumulative effects of an application of navigated transcranial magnetic stimulation to at least one location in a brain, said method comprising the steps of:
   determining a growth function of a stimulation dose in at least one location of a brain, wherein the growth function is derived at least partially according to a known, inferred or estimated tissue type of the at least one location of the brain,
   determining a decay function of the stimulation dose in said at least one location of the brain, wherein the decay function is at least partially derived from a period of elapsed time after the stimulation dose,
   calculating a cumulative stimulation dose for said at least one location of the brain based on the growth function and the decay function at one or more points in time, and
   administering the navigated transcranial magnetic stimulation to the brain, wherein the administering is based at least partially on the calculated cumulative stimulation dose.

12. A method in accordance with claim 11, wherein each location is a three dimensional area of the brain.

13. A method in accordance with claim 11, wherein the determination of the growth function is based at least in part on a predetermined definition, derivative of said predetermined definition or combination of at least two predetermined definitions or derivatives thereof.

14. A method in accordance with claim 13, wherein the predetermined definition is an electric field $\vec{E}$ surrounding a stimulus, or an amplitude of the electric field $|\vec{E}|$, at a location caused by a transcranial magnetic stimulation excitation pulse.

15. A method in accordance with claim 13, wherein the predetermined definition is an induced tissue current density $\vec{J}$, or an amplitude of an induced tissue current density $|\vec{J}|$, at a location, where $\vec{J}=\sigma\vec{E}$ and $\sigma$ is an electric conductivity at the location.

16. A method in accordance with claim 13, wherein the predetermined definition is an induced tissue charge density Q at the at least one location, where $Q=t_r|\vec{J}|$ and $t_r$ is a rise time of the navigated transcranial magnetic stimulation pulse.

17. A method in accordance with claim 13, wherein the predetermined definition is an energy density of an electromagnetic field W dissipated per unit volume at the at least one location, where $W=t_r\sigma|\vec{E}|^2$, $t_r$ is a rise time of a transcranial magnetic stimulation pulse and $\sigma$ is an electric conductivity.

18. A method in accordance with claim 13, wherein the predetermined definition is a temperature increase Q at a location and/or a Specific Absorption Rate SAR at a location, where $$SAR = \frac{\sigma|\vec{E}|^2}{\rho}$$

and $\rho$ is a density at location.

19. A non-transitory computer readable medium comprising software for representing to a user a determined or approximated one or more effects of application of a navigated transcranial magnetic stimulation to a brain of a subject, said non-transitory computer readable medium comprising instructions for:
   determining a growth function of a stimulation dose in at least one location of the brain, wherein the growth function is derived at least partially according to a known, inferred or estimated tissue type of the at least one location of the brain,
   determining a decay function of the stimulation dose in said at least one location of the brain, wherein the decay function is at least partially derived from a period of elapsed time after the stimulation dose,
   calculating a cumulative stimulation dose for said at least one location of the brain based on the growth function and the decay function at one or more points in time, and
   administering the navigated transcranial magnetic stimulation to the brain, wherein the administering is based at least partially on the calculated cumulative stimulation dose.

* * * * *